(12) United States Patent
Katrib et al.

(10) Patent No.: US 6,781,022 B1
(45) Date of Patent: Aug. 24, 2004

(54) POLYVALENT BIFUNCTIONAL CATALYST AND THE PROCESS OF REALIZATION OF SUCH A CATALYST

(75) Inventors: Ali Katrib, Strasbourg (FR); Damien Mey, Strasbourg (FR); Gilbert Maire, Haguenau (FR)

(73) Assignee: Boubyan Petrochemical Company (K.S.C.), Safat (KW)

( * ) Notice: Subject to any disclaimer, the term of this patent is extended or adjusted under 35 U.S.C. 154(b) by 0 days.

(21) Appl. No.: 09/786,791
(22) PCT Filed: Sep. 7, 1999
(86) PCT No.: PCT/EP99/06581
   § 371 (c)(1),
   (2), (4) Date: May 8, 2001
(87) PCT Pub. No.: WO00/13788
   PCT Pub. Date: Mar. 16, 2000

(30) Foreign Application Priority Data

Sep. 9, 1998 (FR) .............................................. 98 11396

(51) Int. Cl.[7] ................................................ B01J 21/06
(52) U.S. Cl. ...................... 585/275; 585/662; 585/664; 502/305; 502/309; 502/321; 502/350
(58) Field of Search ................................. 502/305, 309, 502/321, 350; 585/275, 662, 664

(56) References Cited

U.S. PATENT DOCUMENTS

| | | | | |
|---|---|---|---|---|
| 3,699,134 A | * | 10/1972 | Armbrust et al. ........... | 552/268 |
| 3,893,947 A | * | 7/1975 | Young ......................... | 502/220 |
| 3,994,833 A | | 11/1976 | Jouy et al. | |
| 4,052,417 A | * | 10/1977 | Slinkard et al. ............. | 549/258 |
| 4,129,592 A | * | 12/1978 | Slinkard et al. ............. | 562/549 |
| 4,140,654 A | * | 2/1979 | Yoshioka et al. ............. | 502/63 |
| 4,316,821 A | * | 2/1982 | Bruckman ................... | 502/350 |
| 4,522,936 A | * | 6/1985 | Kukes et al. ................ | 502/249 |
| 2002/0071970 A1 | * | 6/2002 | Elder et al. .................. | 428/702 |

FOREIGN PATENT DOCUMENTS

| | | |
|---|---|---|
| EP | 0 152 918 | 8/1985 |
| EP | 0 534 867 | 3/1993 |
| EP | 0 584 415 | 3/1994 |
| EP | 0 639 553 | * 2/1995 |
| EP | 0 654 458 | 5/1995 |

OTHER PUBLICATIONS

D.C. Vermaire et al.; "The Preparation of Characterization by Temperature Programmed Reduction", *Journal of Catalysis*, vol. 116, No. 2, Apr. 1989 pp. 309–317.

A. Katrib, et al., "Surface Electronic Structure and Isomerization Reactions of Alkanes on Some Transition Metal Oxides", *Surface Science*, vol. 377–379, Apr. 20, 1997, pp. 754–758.

* cited by examiner

*Primary Examiner*—Kiley Stoner
*Assistant Examiner*—Christina Ildebrando
(74) *Attorney, Agent, or Firm*—Young & Thompson

(57) ABSTRACT

The objective of the present invention is a polyvalent bifunctional catalyst and the process of its realization. A catalyst characterized by the fact that it contains, over a $TiO_2$ support, an oxide or a mixture of metallic oxides of $MC_2$ type obtained by reduction of the corresponding $MC_3$ oxides, the metal(s) forming the $MO_2$ oxides are chosen from the group formed by W and Mo.

26 Claims, 2 Drawing Sheets

POLYVALENT BIFUNCTIONAL CATALYST AND THE PROCESS OF REALIZATION OF SUCH A CATALYST

The present invention concerns the field of catalysis, particularly the field of heterogeneous catalysis.

Its object is a catalysis system based on metallic oxides of the $MO_2$ type.

Its object is also the process of obtaining catalytic systems as well as the application of those systems in the chemical industry, especially in petro-chemistry, for the reactions of isomerization, dehydrogenation, hydrogenation and/or in hydrogenolysis of saturated and/or unsaturated organic compounds.

In the chemical industry, most reactions are accelerated by catalysts whose function is to allow the progress of those reactions under conditions of temperature and pressure which are economically profitable.

We already know four major types of catalysts in the field of heterogeneous catalysis or (contact catalysis):

The pure metals($4e$, $5e$, and the $6e$ periods of transition metals)

The oxides of transition metals or of some heavy elements showing several stable oxidation states.

The solid oxides of metals from the two first columns IA and IIA of the periodic table.

The light metals and non-metals from columns IB, IVB, VB (acid oxides)

Within those different categories, we can distinguish two sub-categories according to their way of preparing this system: Bulk catalyst and supported catalyst, i.e. whose active phase is deposited on a support.

In the chemical industry in general, acid oxides (alumina, silica, ofen mixed, zeolites) catalyse mainly the hydration, isomerization, alkylation and cracking of organic molecules.

Certain oxides can catalyse at the same time redox reactions and acido- basic reactions: these are called bifunctional catalysts (reformation of fuels, synthesis of butadiene).

In the petrochemical industry in particular, the use of catalysts in the isomerization process, allows the obtaining of hydrocarbons with high octane number which can be used directly.

However, the catalysts used nowadays for the types of reactions mentioned above, still present a lot of inconveniences, some of which are important.

Indeed, a big part of the known catalysts contain noble metals such as platinum, paladium or iridium. The content, even if.very small, of such metals in the known catalysts, as well as the difficulties in recycling them, explain the very high prices of such systems.

Furthermore, research trying to replace those noble metals by cheaper metals in order to obtain new efficient catalytic compounds has not brought any really satisfying solutions up to now.

In particular, supported metallic catalysts, well-known for their activity in terms of hydrogenolysis and isomenzation, have been the subject of studies on the substitution of noble metals by oxides of transition metals in particular.

However, the physico-chemical performances in terms of conversion, selectivity, life-time and recycling capability of the catalysts proposed at the end of these studies, are not always up to the industrial expectations, which is all the more prejudicial, as a good number of those new catalysts are often usable for a limited number of compounds and for specific reactions. Moreover, the development of a catalyst with the exact objective is generally uncertain, long and expensive.

As far as the bifunctional catalysts are concerned, one has to note that the acid character is brought by the support, which nowadays is usually an acid or chlorated alumina, eventually a zeolithe, whereas the metallic character is brought by a deposited metal. The necessary presence of two active substances leads to problems too, which are all the more important as these active substances are different, problems such as manufacturing, high costs, incompatibility between the materials and their treatment.

The extensive hydrogenolysis properties of tungsten and molybedenum carbides have been clearly demonstrated by A. Katrib et al. Cat. Lett., 38(1996)95, and it has been shown that the presence of oxygen leads to the formation of oxycarbides $WO_xC_y$ type compounds which provide the isomerization catalytic properties to these new systems.

An identification, in particular by X-ray photoelectron spectroscopy of these new systems enabled to identify the active species as $WO_2$ and $MoO_2$ with isomerization properties (A. Katrib et al. J. Electron. Spectro. Relat. Phenomenon. 76(1995)195, and J. Chim. Phys. 94(1997)1923). On the other hand, the existence of the oxycarbide species $WO_xC_y$ has been excluded. Also, it has been shown that the W or Mo pure metals have hydrogenolysis properties, whereas the $WO_3$ and MoO3 trioxides are catalytically inactive concerning saturated hydrocarbos.

Certain research on these trioxides deposited on alumina (W. Grünert et al. J. Cat. 107(1987)522) have shown that the support stabilises the oxide $WO_3$ in terms of a strong metal-support interaction. It is therefore difficult to form $WO_2$, which is responsible for the catalytic activity on such a support.

In the isomeriztion catalysts, we can refer to the works of Martin (C. Martin et al. Cat. Lett. 49(1997)235) which describes the overall technical experiments allowing to characterize this type of catalysts. Moreover. Vermaire and Van Berge (J. Cat. 116(1989)309) have directed their work on the preparation of isomedzation catalysts, emphasizing among others, the influence of the pH, which is less important in the case of $TiO_2$ than on $Al_2O_3$. They also proposed a mehanism allowing to interprete the stoichiometric ratio 1:1 during the adsorption of the $WO_3$ on the sites Ti—O—Ti type, and they have shown the importance of a monolayer of $WO_3$ deposited on $TiO_2$. According to them, this one corresponds to the maximum amount of tungsten which can accurnaate on $TiO_2$ when it is placed for impregnation in a solution of pH=2. However, Rondon, Howalla and Herculs have established that this maximum quantity depends on the pH of the impregnation solution (Surf. Interface Anal. 26(1998)329).

The works of Yamaguchi, Tanaka and Tanabe (J. Cat. 65(1980) 442) have shown that the activity of catalysts based on tungsten studied in their work, reached a limit value for an initial content of $WO_3$ of 8% (molar). This quantity corresponds in fact to the triple of the formerly identified monolayer. They have also correlated activity to the acidity which occurs during the mixing of the two oxides $TiO_2$ and $WO_3$. This acidity of Lewis type is interpreted by the accumulation of positive electrical charges on the tungsten according to the theory established by Tanabe et al. (Bull. Chem. soc. Japan 47(1974)1064). It is then possible, in the presence of water, to obtain the Brönsted acidity.

Finally, Hino and Arata (Bull. Chem. soc. Japan 67(1994) 1472), have prepared solid superacid, by impregnating titanium hydroxide with $WO_3$. It is not really a question of deposition of $WO_3$ on a suport, since the support ($TiO_2$) is obtained by calcining the corresponding hydroxide after impregnation of the tungsten species. The application of these catalysts for the reactions of isomerization has not been considered.

The problem to be solved by the present invention consists therefore in supplying a bifunctional catalyst, which is cheap and stable in function of time, polyvalent and performing.

To this purpose, its object is a polyvalent bifunctional catalyst, characterized by the presence of $MO_2$ type phase, supported on $TiO_2$. This $MO_2$ phase is obtained by the reduction of the corresponding $MO_3$ oxide(s). The metal(s) forming the $MO_2$ oxides are preferably chosen in the group formed by W and Mo.

The invention will be better understood due to the following description which relates to the preferred preparations, which are presented as a non-limited examples, and are explained with reference to the figures attached as enclosures:

Figure 1:
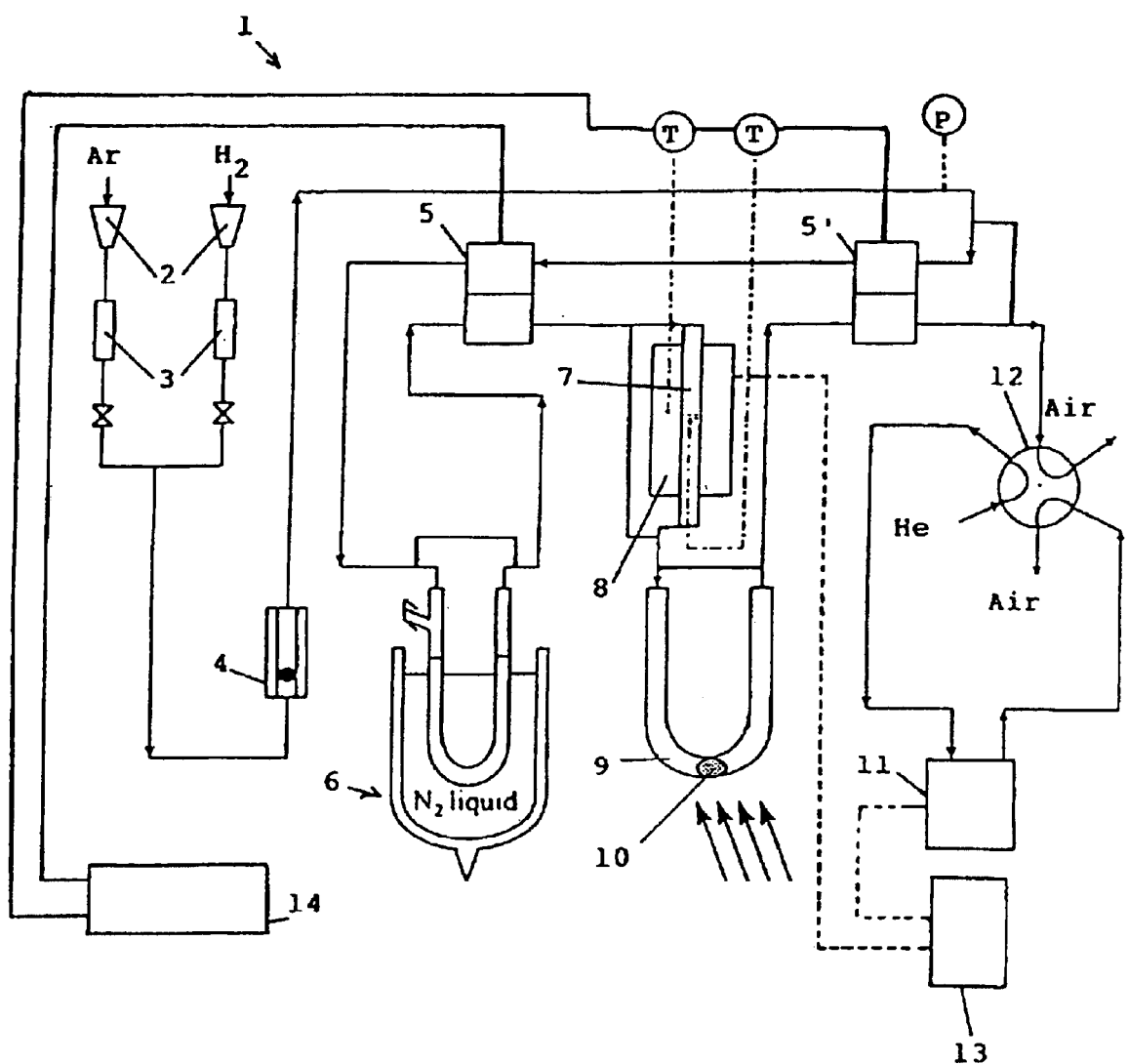
FIG. 1 represents in a schematic way, an example of installation of a reactor plant oriented toward the preparation and the study of the catalyst there after.

According to the invention, the bifuinctional polyvalent catalyst is formed by an oxyde or a mixture of oxides of $MO_2$ type, deposited on a support $TiO_2$. The oxides $MO_2$ being obtained by the reduction of the corresponding $MO_3$ oxides.

The metal(s) forming the $MO_2$ oxides are preferably chosen in the group formed by W or Mo so that the metallic oxide obtained by reduction on its support is the oxide of tungsten $WO_2$ or the oxide of molybdenum $MoO_2$. Of course, mixtures between the oxides of tungsten and molybdenum cited before are possible.

It has been found in a surprising and unexpected way, that a reduction in situ of the initial state of the commercial oxides, $MO_3$ and $MO_2$, is always necessary in order to observe a catalytic activity. Indeed, even by starting with the commercial dioxide $MO_2$ or the metal powder M, there is always a certain number of layers of the corresponding trioxide $MO_3$ present on the surface, which it is necessary to reduce to $MO_2$ in order to observe a catalytic activity.

As a non-limitative example, the isomerizing activity of $WO_2$ can be interpreted by the bifunctional character of this species, in similar way to the supported metallic catalysts.

Indeed, the dioxide behaves like platinum supported on acidic alumina, the $W^{4+}$ ($WO_2$) species having two free electrons, in contrary to $W^{6+}$.

The two free pre-cited electrons lead, from one side, to the formation of σ bonds between the aligned tungsten atoms in $WO_2$. On the other hand, it lead to the formation of π bonds between two tungsten atoms in two neighbouring sites in $WO_2$. The delocalisation of the π electrons acquire the metallic properties to the oxide, which enable the fonctions of hydrogenation and/or dehydrogenation and the dissociation of hydrogen (hydrogen molecule $H_2$).

The pre-cited electrons can be observed as a density of state at the Fermi-level in the X-ray and Ultraviolet photo-electron spectroscopy. Therefore it is possible to distinguish between the presence of two W—W bond lengths in $WO_2$, depending on the presence or not of the π bond. The protonation of the surface oxygen atoms leads to the formation of Bronsted acidic sites within the material. These acidic sites enable the isomerization functions, i.e. the displacement of the hydrocarbon chains.

The choice of $TiO_2$ as a support, is essential for the present invention, and it brings numerous important advantages to the catalytic compounds of the present invention.

Indeed, titanium dioxide is present in two cristalline varieties(A. D. Waddey, rev. pure. Appi. chem. 5(1955)165), called rutile and anatase having a tetragonal structure with slightly different lattice parameters.

The inventors have noticed that the $TiO_2$ rutile structure corresponds to the $WO_2$ (deformed rutile structure) crystal structure. Therefore, the two oxides, $TiO_2$ and $WO_2$ have very close c stuctures with neighbouring geometrical parameters.

According to the present invention, the metallic oxide(s) $MO_3$ reduced to $MO_2$ can be deposited on the $TiO_2$ support alone, or $TiO_2$ supported on a substrate having larger surfine area than $TiO_2$.

We project for example, to deposit $TiO_2$ whose surface area in the orde of 57 $m^2/g$ on the surface of metallic oxides, preferably, $SiO_2$, $Al_2O_3$ or a zeolite, where all these supports have surface areas of the order of 180 $m^2/g$.

The activation of the catalyst, by means of the reduction of the oxide $MO_3$ to $MO_2$ is an essential element of the present invention.

Indeed, initially, the metal, tungsten for example, is present in the state of trioxide $MO_3$ (catalytically inactive) in all the prepared catalysts. Those need therefore a reduction under hydrogen from $MO_3$ to $MO_2$ in order to activate the catalyst. This reduction process is realised directly in the catalytic reactor FIG. 1.

In FIG. 1, one can see that the gases used are initially purified, by circulating on a first trap 2, which reduces the eventual traces of oxygen to water, which is trapped on a zeolithe trap. The outputs are regulated with the help of a volumic debitmeter 3 of tylan type and a debimeter of Brookes 4 for further control.

The gaseous flux circulates first of all through the compartiment of reference of the catharometers 5, 5'. It goes then through a second trap 6, refrigerated by liquid nitrogen for example, at the passage of which an eventual injection of reacting hydrocarbons. The mixture which is made this way passes over catalyst 7, placed in an oven 8. The passage on the catalyst is monitored by two catharometers 5, 5', respectively placed before and after the oven 8. At the outlet of oven 8, a hydrogenator containing heated platinum Adams 10, enables to hydrogenate the unsaturated to saturated hydrocarbons which are analysed by gas chromatography. The physical parameters of the reaction of reduction (temperature, and pressure) are measured by the thermocouple T and the manometer P.

An advantageous realisation of the invention, is that the reduction takes place under a gaseous flux containing at least hydrogen at a temperatures between 380 and 550° C., for at least 6 hours, and a gas flux which ranges between 0.010 l/min and 0.050 l/min, preferably 0.030 l/min. and containing a volume ranging betwen 90% and 100% hydrogen, preferably 99% hydrogen. Under these conditions the catalytic activity stablises within 6 hours.

In another way of realisation, which is particularly practical to determine the reduction temperature at which the catalytic activity stabilises, is for the reduction process to take place under a gaseous flux containing beside hydrogen, a gaseous hydrocarbon reactant which is going to be reacting on the catalyst. As non limitive examples, such gaseous hydrocarbon compounds, we mention 2-methylpentane, n-heptane, 4-methylpentene-1.

Also as an example, the gaseous hydrocarbon can be present in the mixture under a partial pressure ranging between 666.6 Pa(5 torr) and 1999.8 Pa(15 torr), preferably 799.9 Pa(6 torr).

In an advantageous manner, the $MO_3$ oxide(s) are deposited in atomic layers on a support material before being reduced into $MO_2$; that reaction does not affect the number of atomic layers.

In order to obtain the best catalytic results in terms of selectivity and conversion, the number of atomic layers of $MO_2$ present on the support material ranges between 1 and 8 layers, preferably 5. This corresponds in practice to catalysts containing from 5.4% to 27% of mass of $MoO_3$, which is the equivalent of 4.8% to 24% of mass of $MoO_2$ or between 6% to 30% of mass of $WO_3$ which corresonds to 5.7% to 28% of mass of $WO_2$.

In accordance with a first variation of realisation, a catalyst corresponding to the invention is obtained by a simple mechanical mixture of $MO_3$ and $TiO_2$.

So, according to a first process of obtention corresponding to the present invention we follow the following steps:

Preparing a mechanical nxxture of one or several $MO_3$ oxides with $TiO_2$ or $TiO_2$ deposited on a substrate presenting larger specific surface area than $TiO_2$ alone. The mixture having a metal M content ranging between 5% and 25%, and preferably 22%.

Crushing the obtained mixture in the first step.

Reducing, preferably at 460° C., the deposited $MO_3$ oxide(s) to the corresponding $MO_2$ oxide(s) by the introduction of a gaseous flux containing at least hydrogen.

In this manner, the step of depositing the $MO_3$ oxide(s) is realised by mixing mechanically the crushed $MO_3$ oxide(s) with $TiO_2$ or $TiO_2$ deposited on a substrate presenting larger specific surface area than $TiO_2$ alone such as $SiO_2$.

We describe below in more details, an example of the process to obtain a catalyst according to the invention by mixing mechanically $WO_3$ with $TiO_2$.

The catalyst is obtained by crushing in a mortar a mixture of trioxide of tungsten which was calcined for 16 hours and dioxide of titanium (P25-Degussa).

Characterization of the support ($TiO_2$)
Porous volum=0.0005 l/g
Specific area=50 m²/g A first catalyst C1 has been prepared whose content in tungsten corresponds to an atomic layer of $WO_3$ deposited on $TiO_2$. The quantity of the $WO_3$ necessary, is determined on the basis of the parameters of the lattice structure of $WO_3$ according to the values given in table 1 as follows:

TABLE 1

Contents in oxydes and in metal for the catalyst C1.

|  | Masse [g] | Final content in oxide (% mass./% mol.) | Masse of metal (W/Ti) [g] | Content in metal (% mass.) |
|---|---|---|---|---|
| $TiO_2$ | 1 | 92.85%/97.5% | 0.599 | 55.66% |
| $WO_3$ | 0.077 | 7.15%/2.5% | 0.061 | 5.67% |
| Total | 1.077 | 100% | | |

A second catalyst C2 has been prepared by calcining catalyst C1 for 16 hours at 500° C. This treatment of calcination is similar to the treatment of calcination following the impregnation which will be described later. The study of these catalysts has allowed to understand the modifications which can occur during this step of calcination: sintering or diffusion of species in the solid state (Ceramic way).

In a second way of practical preferential realization of the catalyst according to the invention, is a catalyst deposited on a support.

This process of obtaining a catalyst according to this way of preparation is characterized by the following steps:

Washing the raw support, drying and calcination

Crushing the obtained solid followed by sifting (separation of particle sizes).

Depositing the $MO_3$ oxide(s) on a support material made up of $TiO_2$ or $TiO_2$ deposited on a substrate presenting larger specific surface area than $TiO_2$ alone by impregnation of the support material with a solution of one or several salts of the metal M.

Calcination of the obtained product to form $MO_3$ oxyde (s).

Reduction, preferably at 510° C. of the $MO_3$ oxide(s) by introducing a gaseous flux containing at least hydrogen on the $MO_3$ oxide(s).

In a preferred way, only the particles with a diameter ranging from 80 μm to 400 μm were conserved.

In accordance with the invention, the impregnation of the salt(s) of the metal M takes place between 2 to 4 hours, preferably 3 hours, at a temperature ranging from 50° C. to 90° C., preferably 70° C.

In accordance with other characteristics of the invention, one of the salt(s) of tungsten or molybdenum could be used in order to obtain $WO_3$ then $WO_2$ or $MoO_3$ then $MoO_2$, preferrably $(NH_4)_{10}W_{12}O_{41}.5H_2O$ for W and $(NH_4)_6Mo_7O_{24}.4H_2O$.

As will be explained in more details below, the impregnation of the support can be done under a controlled pH or not. Otherwise, according to another characteristic of the invention, the impregnation of the support occurs under a constant pH ranging between 1 and 4, preferably a pH equal to 2.

According to most preferred embodiment of the realisation which will be explained in more details further on, it can be foreseen that the salt solution is in excess with respect to the support volume which is evaporated after the impregnation in an oven at a temperature ranging between 80° C. and 120° C., preferably at 100° C., for 10 to 14 hours, preferably 12 hours.

For all of these processes of-obtention of the present invention, the number of atomic layers of $MO_3$ oxides deposited on the support ranges between 1 to 8, preferaably 5 layers, and as for all catalysts, the metal(s) forming the $MO_2$ oxide(s) in the processes according to the present invention are preferably chosen in the group formed by W and Mo.

In the known processes of dry impregnation one dissolves the precursor in a solution which occupies exactly the porous volume of the treated support. Taking into account the small mass of $TiO_2$ used, and the small porous volume of $TiO_2$ (0.5 cm³/g). A new process of a catalyst by using a technique of impregnation by excess solution is established in this invention.

Such a process of impregnation by excess of a solution is described in the work of Wang and Hall(J. Cat. 77(1982) 232). It consists in eliminating by filtration the excess solution(ammonium paratungstate) which has been in contact with the support.

However, the inventors found that only an impregnation realized with a pH which is sufficiently acid, allows to observe a significative catalytic activity concerning the catalytic products studied in this work.

We are going to describe in more details an example of the process of preparation of a tungsten catalyst supported by wet impregnation at a non-controlled pH.

In this process, the solution containing the precursor occupies a volume which is much bigger than the porous volume alone. The quantities of ammonium paratungstate which are necessary for the deposit one or five layers of $WO_3$, have been dissolved in distilled water; the solutions obtained that way, having been in contact with $TiO_2$. There are two possibilities then:

For the catalyst C3 on which we wished to deposit an atomic layer, the excess of solution has been eliminated by filtration. The catalyst has been dried up in an oven (110° C.) then calcined at 500° C.

For the second catalyst C4 on which to deposit the equivalent of 5 layers, the solution of impregnation has been eliminated by evaporation. This corresponds to the preferred variation of the impregnation process derived from the one proposed by ipatieff et al. The catalyst has been then treated like the precedent one (drying and calcination). The quantities used as an example in catalyst C4 are given in table 2.

TABLE 2

The expected contents in oxydes and metals present in catalyst C4.

| | Mass (oxides) [g] | Content (oxides) | Masses (metal) [g] | content (metal) |
|---|---|---|---|---|
| $TiO_2$ | 1 | 72.2% | 0.599 | 43.24% |
| $WO_3$ | 0.385 | 27.8% | 0.305 | 22.06% |
| Total | 1.385 | 100% | | |

We noted for the catalyst C3 that the theoretical contents of tungsten have only partially been reached: The difference between the theoretical and experimental metal values allows to take into consideration the losses due to the use of this method in the case of the following preparation.

Another technique of impregnation by excess of solution at a controlled pH, is derived from the works of Rondon et al. as well as Wang et al.

We are going to describe below in a more precise way an example of a process of preparation of a tungsten catalyst supported by wet impregnation at a controlled pH.

Preparation of the support: The raw support is first of all washed. Then it is dried followed by calcination at 500° C. The obtained solid is crushed in a mortar; only the particles of diameters ranging from 80 to 400 mm are conserved.

Impregnation: The precursor of the used tungsten is ammonium paratungstate $(NH_4)_{10}W_{12}O_{41}.5H_2O$. The use of this salt allows to lead only to the formation of $WO_3$ after calcination.

Two solutions of ammonium paratungstate 0.005 M, whose initial pH were adjusted respectively to 4 and 2 were prepared by the addition of $NH_4OH$ and 4M of $HNO_3$. 40 ml of each of the two solutions were put in contact, at room temperature and stirred for 5 min., with 8.00 g of $TiO_2$ prepared as explained below:

We were careful to keep the inital values of the pH conserved during the whole duration of impregnation. After that period of impregnation of 3 hours at 70° C., the excess solution was eliminated by evaporation in an oven at a temperature of about 100 to 110° C. for 12 hours. They were then calcined for 15 to 16 hours at 500° C. The catalyst C4 is then obtained from the second solution (pH=2) after reduction at 510° C. for 40 hours.

One has to note that under those conditions, the concentration in metal of the solution of the metallic percursor varies a little during the impregnation. One can note, as an indication, that the fixation of an atomic layer of $WO_3$ leads to a loss in tungsten in the ammonium paratungstate solution of about 10%.

The best catalytic results have been obtained using catalysts prepared following the methode described by "Ipatieff" (J. Am. Chem. Soc. 70(1948)533), in which the excess solution has been eliminated by evaporation.

Of course, the molybdenum catalyst is obtained by the same scheme as the one used in the example of tungsten catalyst.

Catalytical Tests

In order to evaluate the capacities of the prepared catalysts, we have performed a series of catalytic tests using the catalytic reactor presented in FIG. 1, which is equally used for the reduction of the oxides.

A hydrocarbon such as 2-methylpentane has been used in order to determine the reduction temperature which is necessary in order to activate and stabilise the catayst. The reaction temperature is always at 350° C., except when the reduction takes place at lower temperature: In this case, the reaction temperature is the same as the reduction temperature.

The added hydrocarbon to the hydrogen flux is injected in a refrigerated trap by the melted anisole(−37.5° C.), which enables to obtain a partial pressure of the hydrocarbon at about 666.6 Pa (5 torrs). The used hydrogen flux is 0.03 l/min, in order to ensure a passage time of about 6 minutes for the hydrocarbon over the catalyst.

At the reactor exit, the mixture of the hydrogen and the hydrocarbon is analysed by in line gas chromatography. In this order, a capillary column of 50 m length and a 0.53 mm interior diameter was employed. This is diluted by helium (0.00122 l/min, which corresponds to 0.0927 m/s). The stationary phase is dimethylpolysiloxane.

The temperature program applied to the colon is composed of a first level of 20 min at 35° C., followed by a linear increase in the temperature of 25° C./min, then a third level at 110° C. for 30 min.

The chromatograph used in this work is provided with a flame ionization detector, supplied by a mixture of air/hydrogen, and stabilized at 200° C., meanwhile the injector is maintained at 150° C.

The spectrum obtained by gas chromatography is analysed in order to calculate the product distribution, the selectivity and the activity as well as the rate of the reaction.

The study of the C1 and C2 catalysts obtained by mechanical mixture(the amount of tungsten corresponds to a monolayer of $WO_3$ on $TiO_2$)

The study of the catalysts behaviours in which we have applied levels of one hour at increasing temperatures, shows a significant activity at 460° C. reduction temperature. As a result, these catalysts were studied in function of reduction time at 460° C.

Figure 2:
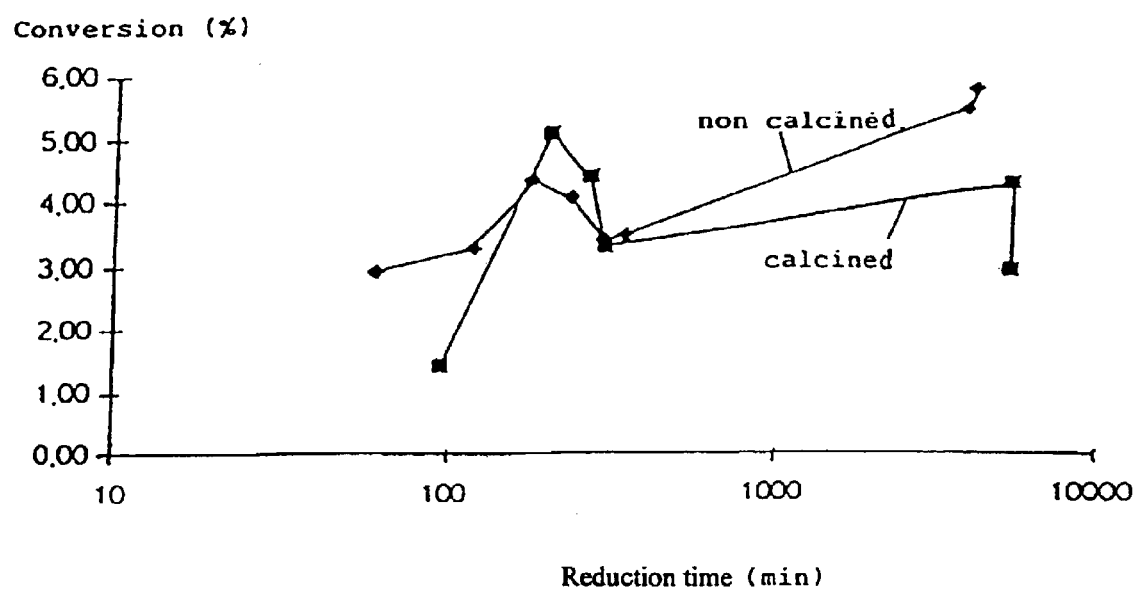
FIG. 2 represents a diagram showing a comparaison between the activities of the calcined and the non-caiined mechanical mixture of the catalysts C1 and C2 in function of the time of reduction using 2-methylpentane reactant.

The diagrams present in FIG. 2 represent the most interesting results concerning the catalyst before and after calcination for 12 hours at 500° C.

FIG. 2 shows also the influence of the calcination step in the preparation of the catalyst which is responsible for the lowering of the activity for longer periods of reduction. However, both catalysts C1 and C2 present a very high selectivity of about 90%.

Study of the the suDported catalyst C3 (deposit of the equivalent of one monolaver of $WO_3$), obtained by impregnation at a non-controlled nH.

As in the precedent cases, the catalyst has first been treated at levels of one hour at increasing temperatures. The catalyst has thus been tested at temperatures ranging between 380° C. and 700° C. However, the inventors did not found values of conversion which were comparable to those obtained by the catalyst C4 studied below.

For that matter it is suitable to note that fact to operate at temperatures as high as 700° C. can lead to the obtenion of $TiO_2$ in the rutile state.

Study of the supDorted catalyst C4. obtained bv impregnation at a controlled pH and bv evanoration of the excess solution.

Figure 3:
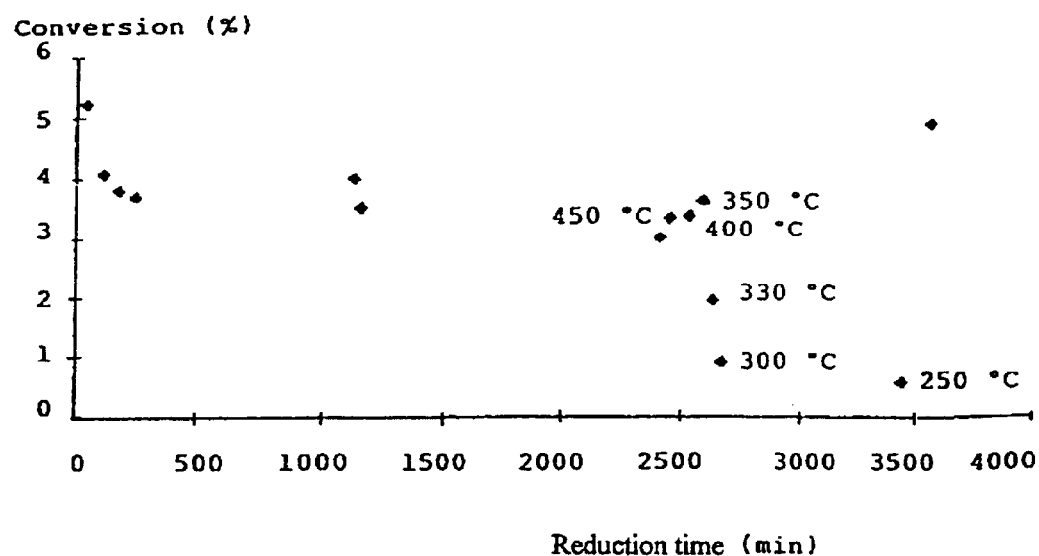
FIG. 3 represents a diagram showing the activity level and the stabilisation of the catalyst C4 using 2-methylpentane reactant.

Catalytical tests (FIG. 3) have also been realised under hydrogen flux, on 50 mg of catalyst, and a partial pressure pressure of 2-methylpentane of 893.3 Pa (6.7 torr). The reaction temperature at the beginning was 350° C. In a first step, the evolution of the surface in function of the time of reduction up to 2400 minutes was studied. In FIG. 3, certain points of measurements correspond to temperatures of reduction different from 460° C., that temperature being then reported on the diagram.

In a second step, the activity at successive levels, at decreasing temperatures from 500 to 250° C. was measured.

Otherwise, the activity of the catalyst C4 was also tested for the isomerization of 4-methylpentene-1(see table 4).

When the metallic mass was increased to 22% of tungsten, which is equivalent to 5 atomic layers (catalyst 4), the observed values for the coversion and selectivity were 8% and 95% respectively. At an equal metallic mass, the impregnation of the support at an acidic pH enables to increase the conversion.

Furthermore, it is possible to reach all the values of conversion between 0 and 75% by varying the temperature of reaction between 300 and 500° C. ***This associates withy a decrease in the selectivity in isomerization: At very low rates of conversion, the isomerization reaches 100%, whereas it is only 4.5% at 510° C. for a conversion of 75% (table 3).

Once the catalyst is prepared under hydrogen at a given temperature of reduction, different products can be obtained for a given reactant by changing only the temperature of the reaction.

EXAMPLE 1

Catalyst C4 (5 layers) Prepared After Reduction Under Hydrogen at 500° C. for 40 Hours Using 2-methylpentane.

The results are summarized in the following table:

TABLE 3

Evolution of the activity and the selectivity in function of the reaction temperature for the catalyst C4 (5 layers).

| T reaction° C. | Activity % | Selectivity in isomers % |
|---|---|---|
| 350 | 8 | 95 |
| 330 | 3.6 | 97 |
| 300 | 1.2 | 100 |
| 315 | 2.3 | 98 |
| 380 | 12 | 81 |
| 350 | 8 | 94 |

TABLE 3-continued

Evolution of the activity and the selectivity in function of the reaction temperature for the catalyst C4 (5 layers).

| T reaction° C. | Activity % | Selectivity in isomers % |
|---|---|---|
| 400 | 15 | 68 |
| 420 | 16 | 49 |
| 460 | 26 | 15 |
| 510 | 75 | 4.5 |

The temperatures indicated in table 3 are classified in chronological order from the bottom, the first temperature (350° C.) corresponding therefore to the first tested temperature of the reaction.

We can observe that returning to 350° C. (6th value) leads to the same values of activity in isomerization (respectively 8% and 94% versus 8% and 95%), found for the reaction temperature during the first measurement: The catalytic system is therefore perfectly stable.

EXAMPLE 2

Catalyst C4 ($WO_3$, (5 layers)/$TiO_2$: Using 4-methylpentene-1 Reactant

The results concerning the evolution of the activity and the selectivity in function of the reaction temperature for the catalyst C4 using 4-methylpentene-1 reactant are summnarized in table 4.

TABLE 4

Evolution of the activity and selectivity in function of the reaction temperature using catalyst C4.

| T reaction ° C. | Activity % | Selectivity in isomers % |
|---|---|---|
| 350 | 58 | 92 |
| 250 | 57 | 90 |

As we can see from the results given in the following tables 5 and 6, that comparable results were obtained by using the $MoO_3/TiO_2$.

TABLE 5

Conversions and selectivities of $MoO_2$, $MoO_3$, and $MoO_3/TiO_2$ for the n-hexane reactant at different reaction temperatures.
[1] = Commercial compounds prior to reduction;
[2] = The initial state in order to obtain the catalyst by impregnation

| Temp. de reaction ° C. | Conversions % | | | Selectivities % | | |
|---|---|---|---|---|---|---|
| | $MoO_2$[1] | $MoO_3$[1] | $MoO_3/TiO_2$[2] | $MoO_2$[1] | $MoO_3$[1] | $MoO_3/TiO_2$[2] |
| 280 | 2.0 | 3.9 | 3.7 | 100 | 97.4 | 100 |
| 300 | 5.5 | 8.2 | 15.2 | 100 | 94.3 | 98.8 |
| 320 | 15.9 | 16.1 | 24.1 | 94.4 | 86.4 | 82.9 |
| 340 | 24.3 | 20.2 | 37.1 | 82.0 | 84.8 | 75.1 |
| 360 | 41.7 | 34.7 | 64.7 | 69.1 | 77.4 | 57.1 |
| 380 | 50.0 | 47.4 | 69.9 | 67.1 | 61.5 | 43.2 |
| 400 | 68.1 | 63.3 | 86.5 | 48.3 | 46.0 | 22.7 |

In the following table 6, the compounds C1 to C5 do not designate the ctatlyst of the present invention but the products of the reaction (five carbon atoms C5 . . . ) of n-hexane. On the other hand, the other abbreviations given in the table are: 22 DMP is 2,2-dimethylpentane, 23DMP is 2,3-dimethylpentane, 2MP is 2-methylpentane, 3MP is 3-methylpentane.

TABLE 6

Products distribution obtained by the reaction of n-hexane on $MoO_3/TiO_2$ at different reaction temperatures.

| Products | Reaction temperatures, °C. | | | | | | |
|---|---|---|---|---|---|---|---|
| | 400 | 380 | 360 | 340 | 320 | 300 | 280 |
| Cracking | | | | | | | |
| C1 | 26.2 | 18.1 | 13.5 | 8.7 | 6.1 | 0 | 0 |
| C2 | 18.6 | 12.1 | 9.5 | 4 | 2.9 | 0 | 0 |
| C3 | 19 | 14.7 | 10.7 | 6.1 | 3.6 | 1.3 | 0 |
| C4 | 8.8 | 6.7 | 5.1 | 2.8 | 1.5 | 0 | 0 |
| C5 | 4.7 | 5.3 | 4.7 | 3.3 | 3 | 0 | 0 |
| Isomerization | | | | | | | |
| 22DMP | 1 | 1.4 | 2 | 1.8 | 2.2 | 0 | 0 |
| 23DMP | 2.3 | 4.3 | 5.5 | 6.3 | 6.1 | 6.3 | 7.3 |
| 2MP | 11.1 | 22.3 | 30.3 | 41.7 | 47.3 | 59.7 | 64.4 |
| 3MP | 7.7 | 14.9 | 19.7 | 25.4 | 27.7 | 34.8 | 36.4 |
| 2MP/3MP | 1.5 | 1.5 | 1.5 | 1.6 | 1.7 | 1.7 | 1.8 |

The catalysts of the present invention are particularly useful in the field of organic chemistry and in particular in petrochemistry.

The catalysts described in the present invention can intervene in isomeization, dehydrogenation, and/or hydrogenolysis reactions of saturated organic compounds, in particular of alkanes as well as in the isomerization, hydrogenation, dehydrogenation, and/or hydrogenolysis reactions of mono or poly-insaturated organic compounds, in particular alkenes and alkynes.

Of course, the invention is not limited to the embodiments described and presented in the drawings given as enclosures. Modifications are possible, especially from the point of view of the use of different elements or by substitution of equivalent techniques, without being outside the field of protection of the invention.

What is claimed is:

1. A polyvalent bifunctional catalyst, characterized by the fact that said catalyst comprises, deposited on a support $TiO_2$, an oxide or a mixture of metallic oxides of $MO_2$ type prepared by the reduction of the corresponding $MO_3$ oxide(s), and wherein said polyvalent bifunctional catalyst has a metallic-acidic surface that can catalyze at the same time redox reactions and acid-base reactions.

2. A catalyst corresponding to claim 1, characterized by the fact that the metal(s) forming the oxide(s) are chosen from the group formed by W and Mo.

3. A catalyst corresponding to claim 1, characterized by the fact that the metallic oxide obtained by reduction on the support is $WO_2$.

4. A catalyst corresponding to claim 1, characterized by the fact that the metallic oxide obtained by reduction on the support is $MoO_2$.

5. A catalyst corresponding to claim 1, which is characterized by the fact that the metallic oxide(s) $MO_3$ which are reduced to $MO_2$ are deposited on a support $TiO_2$ which itself could be deposited on a substrate having larger surface area than $TiO_2$.

6. A catalyst corresponding to claim 5, characterized by the fact that the said substrate is selected from the group consisting of $SiO_2$, $Al_2O_3$ and a zeolite.

7. A catalyst corresponding to claim 1, characterized by the fact that the reduction process takes place under a gaseous flux containing at least hydrogen at temperatures between 380° C. and 550° C., during at least 6 hours, at a flow rate between 0.010 l/min and 0.050 l/min, preferably 0.030 l/min, with a volume between 90% and 100% of hydrogen.

8. A catalyst corresponding to the claim 7, characterized by the fact that the reduction take place under a gaseous flux containing hydrogen and a gaseous hydrocarbon compound which undergoes a chemical reaction using this catalyst.

9. A catalyst corresponding to claim 8, characterized by the fact that the gaseous hydrocarbon is present under a partial pressure range between 666.6 Pa and 1999.8 Pa.

10. A catalyst corresponding to claim 1, characterized by the fact that the oxide(s) $MO_3$ are deposited in atomic layers on a support before being reduced to $MO_2$, this reduction process having no effect on the number of layers.

11. A catalyst corresponding to claim 10, characterized by the fact that the number of atomic layers of $MO_2$ present on the surface of the support ranges between 1 to 8.

12. A catalyst corresponding to claim 1, characterized by the fact that it contains in weight 5.4% and 27% of $MoO_3$, which corresponds to 4.8% to 24% in weight of $MoO_2$.

13. A catalyst corresponding to claim 1, characterized by the fact that it contains in weight between 6% and 30% of $WO_3$, which corresponds to 5.7% to 28% in weight of $WO_2$.

14. A process for obtaining a catalyst according to claim 1, comprising:

preparing a mechanical mixture from one or many $MO_3$ oxides with $TiO_2$ alone or $TiO_2$ deposited on a substrate having larger surface area than $TiO_2$, this mixture containing an amount of the metal M which varies between 5% and 25%, crushing the mixture prepared in the previous step, and reducing at 460° C. the oxide(s) $MO_3$, thus deposited as corresponding $MO_2$ oxides under a flux of a gas containing at least hydrogen over the oxides $MO_3$.

15. The process according to claim 14, characterized by the fact that the step of depositing the oxide(s) $MO_3$ takes place by mechanically mixing the crushed $MO_3$ oxide(s) with $TiO_2$ or $TiO_2$ deposited on a substrate having larger specific surface area than $TiO_2$.

16. The process according to claim 1, comprising:

washing the crude support, followed by drying and calcination, crushing the obtained solid, then sieving it, depositing the $MoO_3$ oxide(s) on the $TiO_2$ support or $TiO_2$ deposited on a substrate having larger surface area than $TiO_2$ by impregnating the so called support with a solution metal M salt(s), calcinating the obtained product in order to form the $MO_3$ oxide(s), and reducing preferably at 510° C. the $MoO_3$ oxide(s) to the corresponding $MO_2$ oxides by passing a gaseous flux containing at least hydrogen over the $MoO_3$ oxide(s).

17. The process according to claim 16, characterized by the fact that only the particles diameters vary between 80 μm and 400 μm are kept following sieving.

18. The process to claim 16, characterized by the fact that the impregnation of the metal M salt(s) takes place for 2 to 4 hours, preferably 3 hours, at temperatures between 50° C. to 90° C.

19. The process according to claim 16, characterized by the fact that in order to obtain $WO_3$ then $WO_2$ a tungsten salt, is used.

20. The process according to claim 16, characterized by the fact that in order to obtain $MoO_3$, $MoO_2$ a molybdenum salt, is used.

21. The process according to claim 16, further comprising impregnating a support material at a constant pH which is in the range between 1 and 4.

22. The process according to claim 21, characterized by the fact that the metal salt solution is in excess with respect to the support which is impregnated, the excess of the solution being evaporated in an oven after impregnation at temperatures in the range between 80° C. and 120° C., for 10 to 14 hours.

23. The process according to claim 14, characterized by the fact that the number of atomic layers of $MO_3$ present on the surface of the support ranges between 1 to 8.

24. The process according to claim 14, characterized by the fact that the metal forming the oxides $MO_2$ are selected in the group formed by W and Mo.

25. A method of increasing the rate of a chemical reaction, comprising:

adding a catalyst corresponding to claim 1, characterized by the fact that this catalyst is added in a reaction of isomerization, hydrogenation, dehydrogenation and/or hydrogenolysis od saturated hydrocarbons.

26. A method of increasing the rate of a chemical reaction, comprising:

adding a catalyst corresponding to claim 1, characterized by the fact that this catalyst is added in a reaction of isomerization, dehydrogenation, hydrogenation and/or hudrogenolysis of mono or poly unsaturated hydrocarbons.

* * * * *

UNITED STATES PATENT AND TRADEMARK OFFICE
CERTIFICATE OF CORRECTION

PATENT NO. : 6,781,022 B1 Page 1 of 1
DATED : August 24, 2004
INVENTOR(S) : Ali Katrib et al.

It is certified that error appears in the above-identified patent and that said Letters Patent is hereby corrected as shown below:

Title page,
Item [57], ABSTRACT,
Line 4, change "$MC_2$" to -- $MO_2$ --.
Line 5, change "$MC_3$" to -- $MO_3$ --.

Signed and Sealed this

Eighteenth Day of January, 2005

JON W. DUDAS
*Director of the United States Patent and Trademark Office*